(12) United States Patent
Hellstrom et al.

(10) Patent No.: US 8,060,234 B2
(45) Date of Patent: Nov. 15, 2011

(54) ACCURATE TRACKING OF WEB FEATURES THROUGH CONVERTING PROCESSES

(75) Inventors: Ake Hellstrom, Columbus, OH (US); Tommi Huotilainen, Helsinki (FI); Antti Saarela, Vihti (FI)

(73) Assignees: ABB Oy, Helsinki (FI); ABB Ltd., Dublin (IE)

( * ) Notice: Subject to any disclaimer, the term of this patent is extended or adjusted under 35 U.S.C. 154(b) by 576 days.

(21) Appl. No.: 12/236,606

(22) Filed: Sep. 24, 2008

(65) Prior Publication Data

US 2009/0088889 A1 Apr. 2, 2009

Related U.S. Application Data

(60) Provisional application No. 60/995,569, filed on Sep. 27, 2007.

(51) Int. Cl.
*G06F 19/00* (2011.01)

(52) U.S. Cl. ........ 700/128; 700/110; 700/122; 700/127; 382/141

(58) Field of Classification Search .................. 700/122, 700/108–110, 124, 125, 127, 128; 382/141, 382/143, 149; 235/494; 162/204
See application file for complete search history.

(56) References Cited

U.S. PATENT DOCUMENTS

| 5,628,574 | A | 5/1997 | Crowley | |
|---|---|---|---|---|
| 6,814,514 | B2 * | 11/2004 | Korngold et al. | 400/621 |
| 6,950,547 | B2 * | 9/2005 | Floeder et al. | 382/143 |
| 7,027,934 | B2 * | 4/2006 | Skeps et al. | 702/35 |
| 7,187,995 | B2 * | 3/2007 | Floeder et al. | 700/122 |
| 7,542,821 | B2 * | 6/2009 | Floeder et al. | 700/124 |
| 7,623,699 | B2 * | 11/2009 | Floeder et al. | 382/149 |
| 2002/0030704 | A1 | 3/2002 | Korngold et al. | |
| 2007/0119518 | A1 | 5/2007 | Carman et al. | |

FOREIGN PATENT DOCUMENTS

| EP | PCT/US2008/077446 | 9/2008 |
|---|---|---|
| JP | 6115803 | 4/1994 |
| WO | WO03/087794 | 10/2003 |

\* cited by examiner

*Primary Examiner* — Dave Robertson
(74) *Attorney, Agent, or Firm* — Michael M. Rickin

(57) ABSTRACT

There is described a method and apparatus for tracking the location of web features through a converting process, one application of which can involve tracking paper defects from a paper machine as detected by a camera system, to a winder where the sheet is wound to rolls so that the web defects can be repaired in the winder before making the rolls. The method to track web features is based on pattern identification of inherent sheet variability or defects. The apparatus involves two or more sheet property or defect monitoring web sensors arranged at the same cross directional location at different stages of the converting operation, augmented by tachometers and/or roll diameter sensors. A full automation system for drive control on the winder based on this information is preferably added to make maximum advantage of this information.

20 Claims, 13 Drawing Sheets

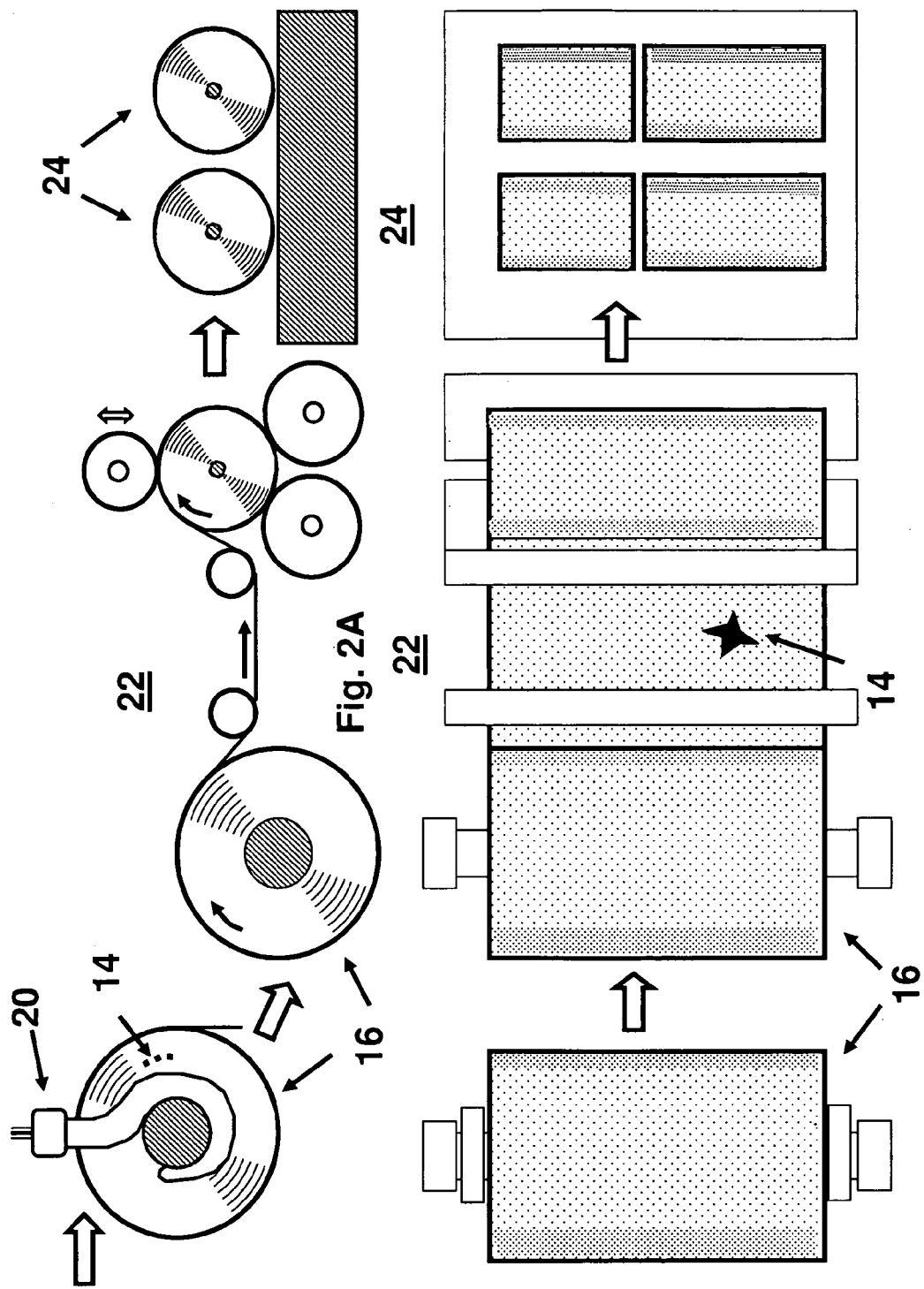

ACCURATE TRACKING OF WEB FEATURES THROUGH CONVERTING PROCESSES

CROSS REFERENCE TO RELATED APPLICATION

This application claims the priority of U.S. provisional patent application Ser. No. 60/995,569 filed on Sep. 27, 2007, entitled "Accurate Tracking Of Web Features Through Converting Processes" the contents of which are relied upon and incorporated herein by reference in their entirety, and the benefit of priority under 35 U.S.C. 119(e) is hereby claimed.

FIELD OF THE INVENTION

This invention relates to the tracking of features of a moving web through a converting process and more particularly to the accurate tracking of those features.

DESCRIPTION OF THE PRIOR ART

In some web processing and converting, for instance paper making and winding rolls of paper, there is a need to locate and repair serious web defects, for instance holes or lumps. This is particularly important if the paper roll is to undergo a subsequent coating or similar converting operations, where even a small hole in the web may catch and cause a sheet break.

Other problems in web processing and converting includes tracking of abnormal variability or property changes of the web, for instance when there is a machine upset or a grade change. In this instance, sometimes more than necessary of the production must be scrapped for such an upset, or there might arise a risk for shipping a bad roll.

The two paragraphs directly above describe examples of problems that may occur in a web. These problems are referred to hereinafter as a defect.

When a major defect is detected by a web inspection system, it is essential that the machine location of this event within the reel is determined. This information is subsequently utilized to stop the winder at the location of the defect to offer operators an opportunity to repair the web. The methods currently deployed for this task have edge marking systems using an ink sprayer such as those sold by R.K.B. Opto-Electronics, Inc. of Syracuse, NY and RYECO of Marietta, Ga., in the paper machine connected to the web inspection system. At the detection of a defect, the ink sprayer is momentarily energized and the edge of the paper is colored to highlight the defect location. This mark is later observed in the winder and the operator has to reduce the machine to a slow speed, allowing manual observation and final search for the defect, and to eventually stop the winder at the defect for repair.

Various enhancements have been suggested including optical detectors in the winder for the color markings, and improvements to the ink spraying mechanism, but no solution has proven long term reliability and is operator friendly. Furthermore, the paper quality may degrade due to ink overspray and dripping, or a clogged ink nozzle may fail to spray and thus leave a defect unmarked in the roll. Also the ink spraying system needs regular maintenance, for example, the cleaning of the ink spraying jets, which if not either timely or properly performed will impair the effectiveness of the system.

Camera based inspection systems, for example the "ULMA" system sold by ABB, are utilized to detect web defects. On-line quality control gauging systems, for example, the ABB "Smart Platform" and "Smart Sensors", are utilized to measure web quality parameters. Drive systems, for example, the ABB ACS600 drive, provide speed, tension and position control for the web processing on the winder. However, there is a missing link in order to provide full automation for the winder. Current ink marking systems and manual observation of the colored edge still puts the responsibility on the operator to search for the actual defect location in the rewinding operation. A solution that connects these systems and provides a fully automated and accurate stop of the winder at the defect location is desired. The present invention provides that solution.

SUMMARY OF THE INVENTION

A system for locating a defect of a moving sheet having naturally varying properties during first and second sheet making processes. The system has a processor capable of executing code stored on a non-transitory medium. The code configured to:

process a first digital representation of one lane of a reel produced from the moving sheet during the first sheet making process and a second digital representation of the one lane of the sheet during the second sheet making process;

obtain from the first digital representation a first pattern of the naturally varying properties of said moving sheet during the first sheet making process;

obtain from the second digital representation a second pattern of the naturally varying properties of the moving sheet during the second sheet making process; and locate the sheet defect during the second sheet making process by correlating the first and second patterns.

A method for tracking features of a moving sheet. The method has the steps of:

detecting a defect in the sheet during a first sheet making process;

obtaining a first pattern of the naturally varying properties of the sheet during the first sheet making process;

obtaining a second pattern of the naturally varying properties of the sheet during a second sheet making process; and locating the defect during the second sheet making process by correlating the first and second patterns.

A computer program product stored on a non-transitory media for tracking features of a moving sheet having naturally varying properties. The computer program product has computer usable program code configured to obtain a sheet defect signal during a first sheet making process. The computer usable program code is also configured to obtain a first pattern of the naturally varying properties of said moving sheet during said first sheet making process. The computer usable program code is further configured to obtain a second pattern of the naturally varying properties of the moving sheet during a second sheet making process and to locate the sheet defect during the second sheet making process by correlating the first and the second patterns.

DESCRIPTION OF THE DRAWING

FIG. 2A shows the elevation and FIG. 2B the top view of a typical winder operation.

DETAILED DESCRIPTION

The present invention has several embodiments. In one embodiment, a laser and a detector are used to generate an optical signature of one lane of the reel produced by the web making machine. In another embodiment, the information from a camera based web inspection system is used to generate the optical signature. Each of these embodiments are described below.

Figure 1A:
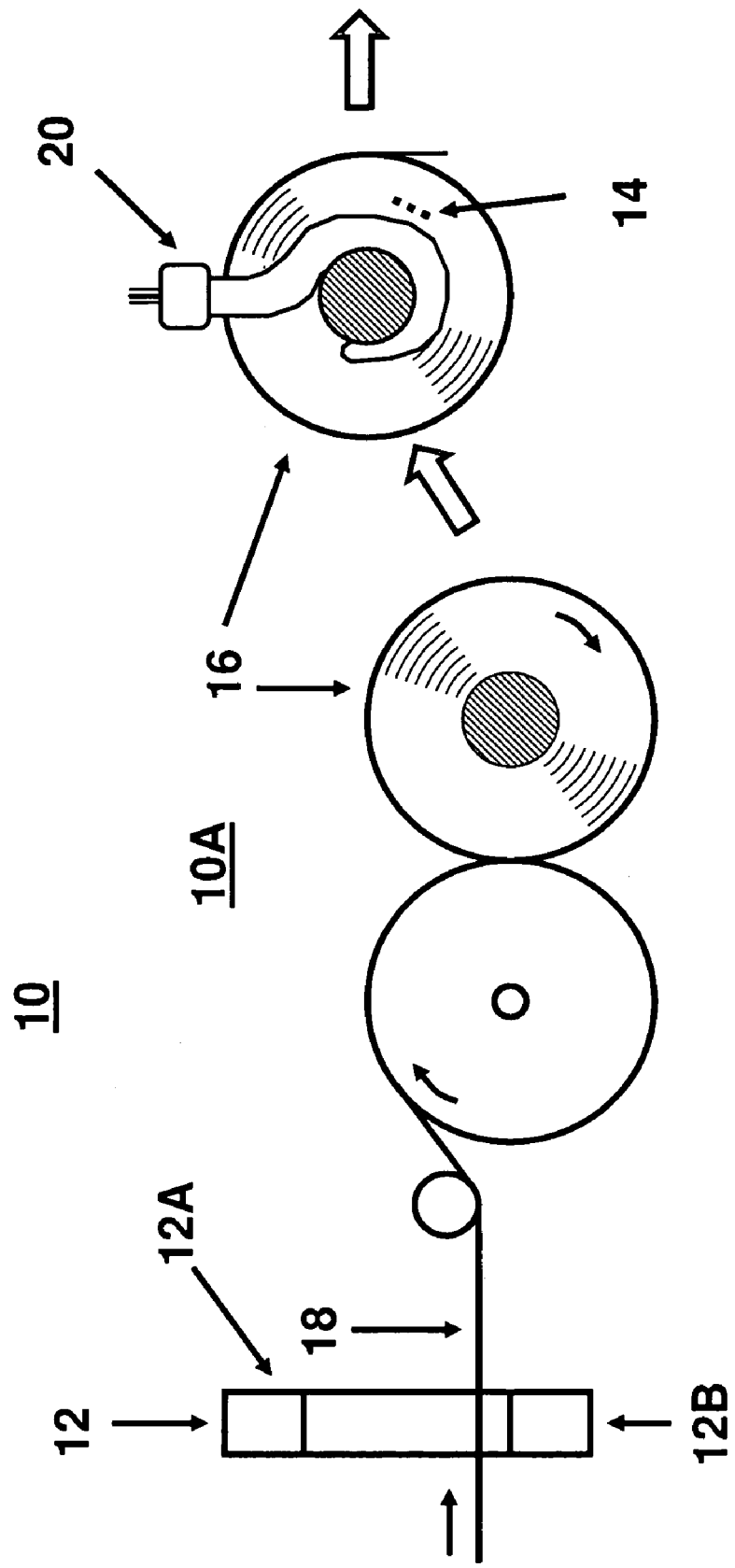
FIG. 1A shows the elevation and FIG. 1B shows the top view of the reel end of a paper machine 10 including a web inspection station.
Figure 1B:
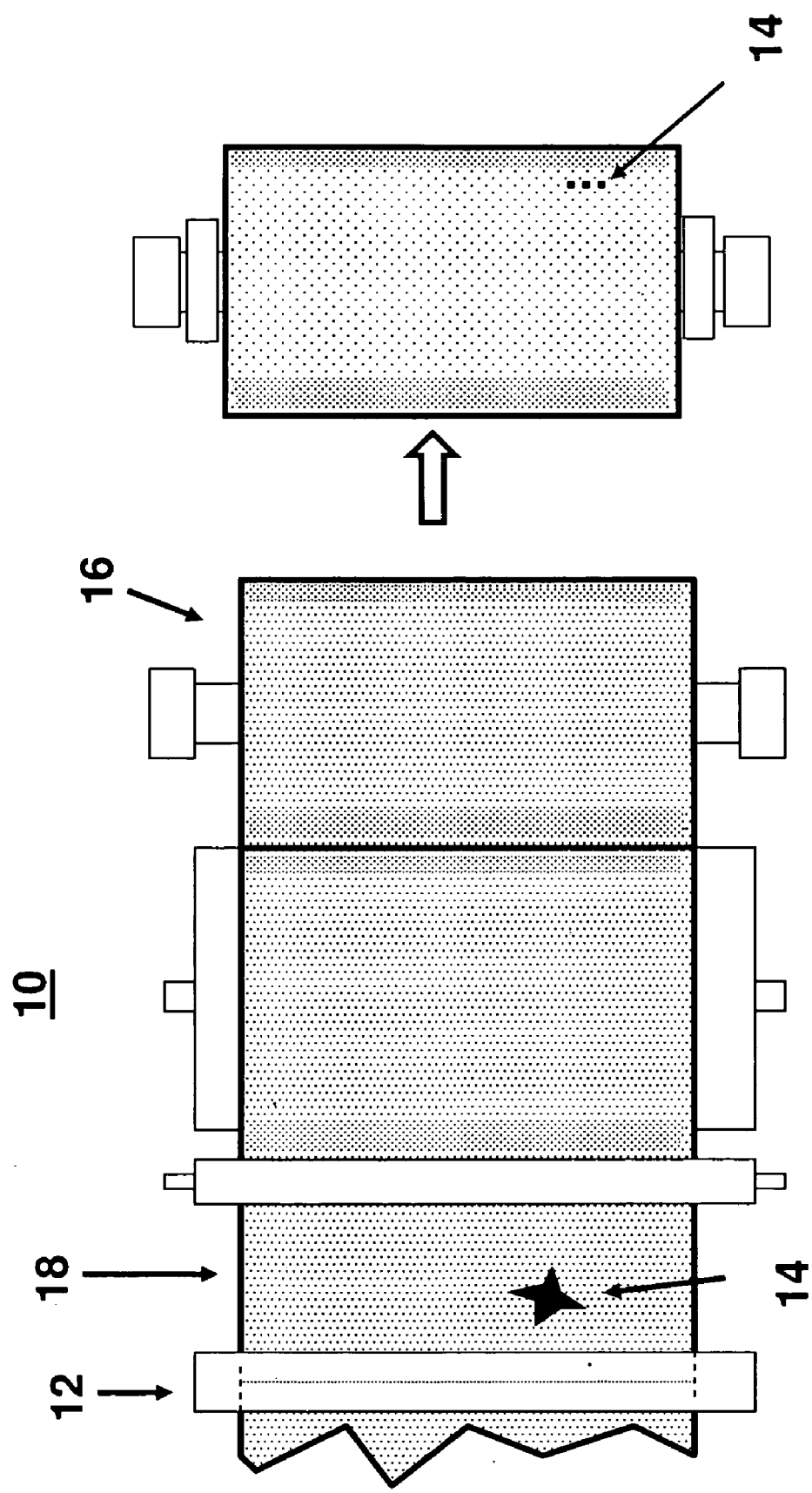

FIG. 1A shows the elevation and FIG. 1B shows the top view of the reel end 10A of a paper machine 10 including a web inspection station 12. Station 12 includes a line camera 12A and a light source 12B. A defect 14 inside the reel 16 is schematically illustrated in FIG. 1B on the web 18. When the reel 16 is complete, it is lifted with a crane 20 to be transferred to the winder 22 shown in FIGS. 2A and 2B. The reel 16 will, as shown in FIG. 2A, contain somewhere inside its bulk the web defect 14.

FIG. 2A shows the elevation and FIG. 2B the top view of a typical winder operation 22. The reel 16 from the paper machine is rewound into paper rolls 24, or to form another reel (not shown) for coating, treatment or converting. As part of the re-winding operation, the winder 22 must be slowed down and stopped at a paper defect 14 so the operators can repair the web defect, and the re-winding can resume only when the repair is complete. The winder 22 operates normally at a very high speed and must be brought down to a creep speed when approaching the area in which the defect 14 is believed to be located to allow the operators to visually find the defect 14.

The web inspection system 12 on the paper machine has a very fast speed of response and can accurately determine the time when a defect 14 is detected. This time must be translated to a machine direction web location assigned to the reel 16 in order to track this location to the winder 22. This tracking is made more complex by the fact that machine speed and winder speed are different and some paper is lost on the top of a reel due to slab-off losses for paper lab sampling, to clean off the reel, and to remove bad external wraps of paper. Thus, there is a need to accurately transfer machine direction coordinates from the paper machine 10 to the winder 22 despite the lost paper.

This invention compares the signature in the same cross directional direction area, from the paper machine 10 to the winder 22, which is one example of a converting process, or between any other steps in the converting process. Typically, this signature can be established by information in existing optical web inspection cameras, or by other optical transmission sensors based on, for example, lasers and detectors. This signature composed of small-scale variability as well as large-scale variability is unique and thus it can be used to positively identify the machine location of an event or defect and achieve position synchronization between two different process locations equipped with similar transmission measurements. By recording the paper signature on the paper machine 10 and defining a defect location relative to this signature, it will be possible to slow down and stop the winder 22 ahead of the defect by monitoring the same signature on the winder.

Figure 6:
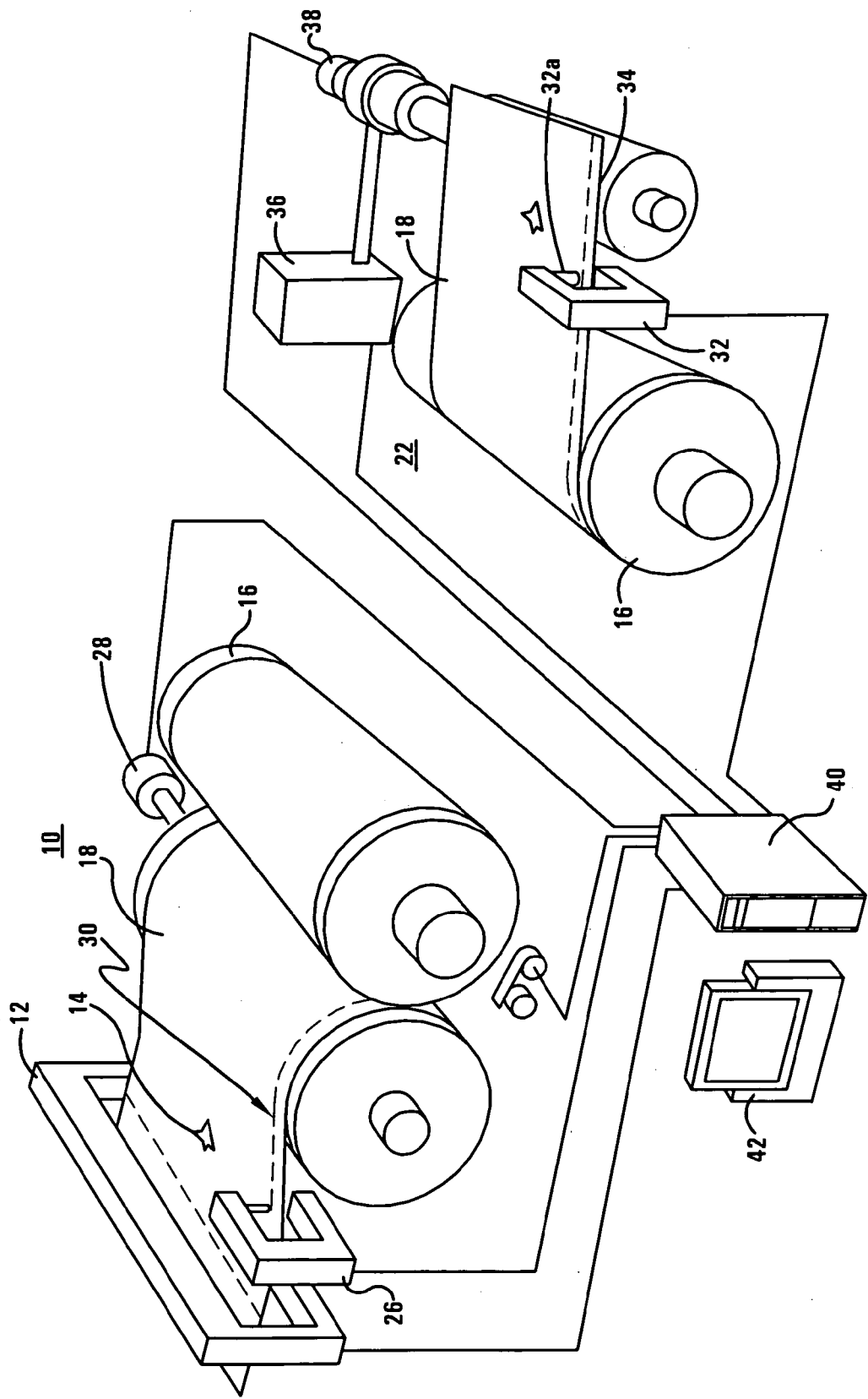
FIG. 6 shows the embodiment of the present invention in which a laser and detector are used to obtain the signature.
Figure 7:
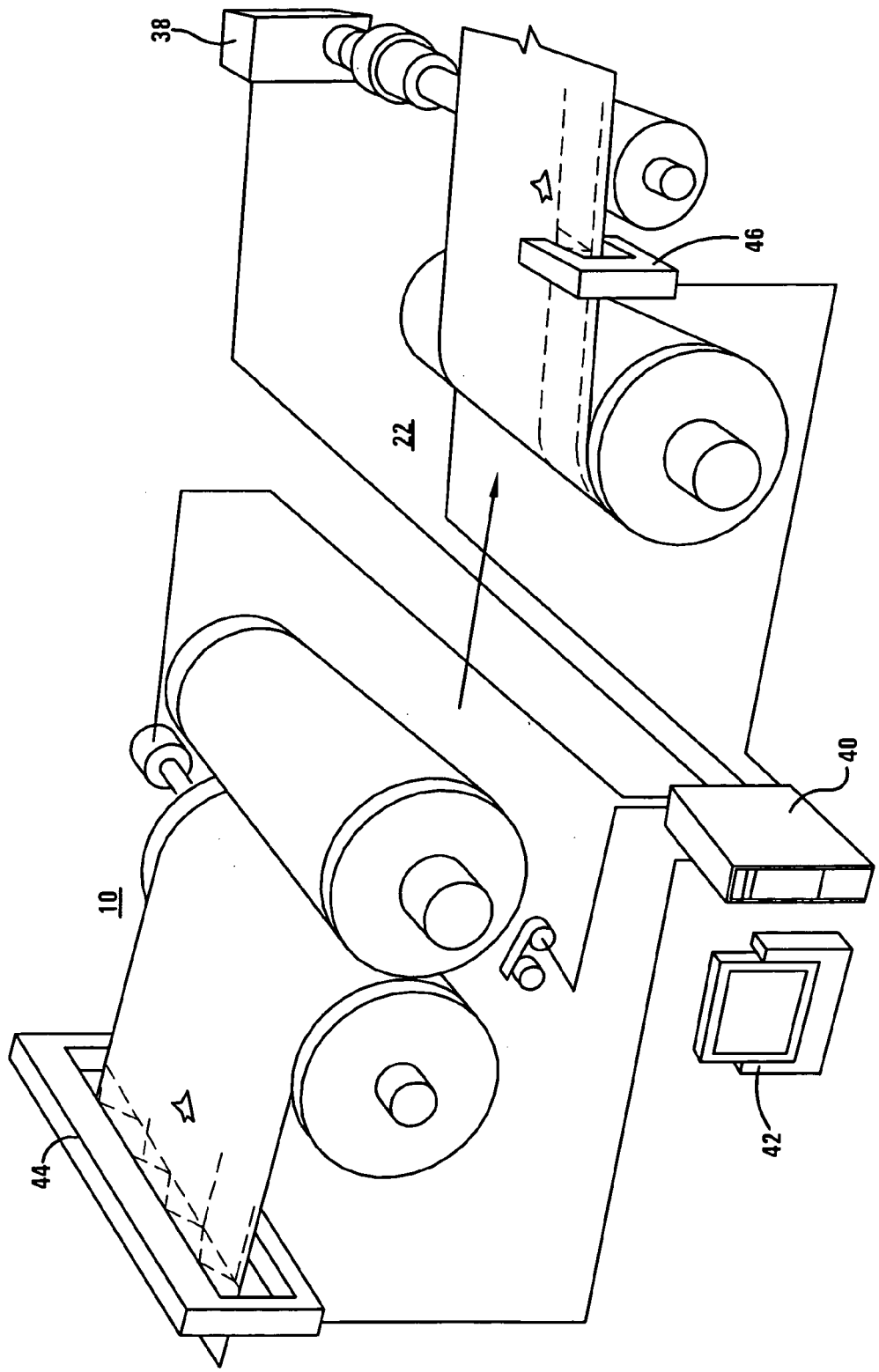
FIG. 7 shows the embodiment of the present invention in which a web inspection camera is used to obtain the signature.

FIG. 6 shows the embodiment of the present invention in which a laser and detector are used to obtain the signature and FIG. 7 shows the embodiment of the present invention in which a web inspection camera is used to obtain the signature. For ease of description, the same element in both figures is given the same reference numeral.

Figure 3B:
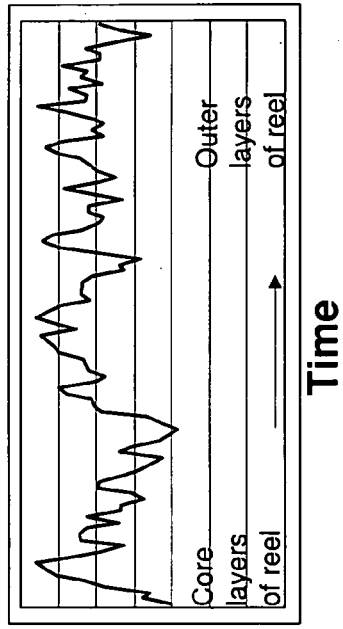
FIG. 3B shows an optical signature of one lane of the reel being produced in the paper machine.
Figure 3A:
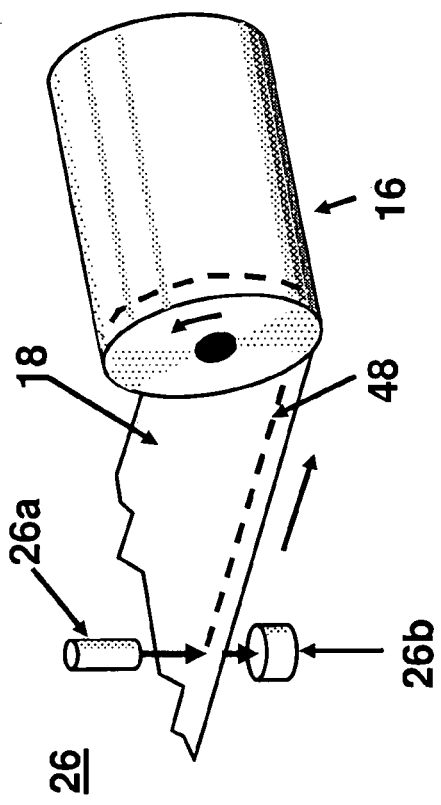
FIG. 3A shows a laser on one side of a moving web and a detector on the other side of the moving web directly below the laser.

Referring now to FIG. 6, the paper making machine 10 includes a web inspection system 12 followed immediately by an optical transmission sensor 26 that is located along the edge 30 of moving web 18. The sensor 26 has as is shown in FIG. 3A, a laser 26a that is located on one side of the moving web 18 and a detector 26b that is located on the other side of the moving web 18 and directly below the laser 26a. The web 18 has a defect 14 shown symbolically in FIG. 6. The paper making machine also includes a reel pulse tachometer 28.

Figure 4B:
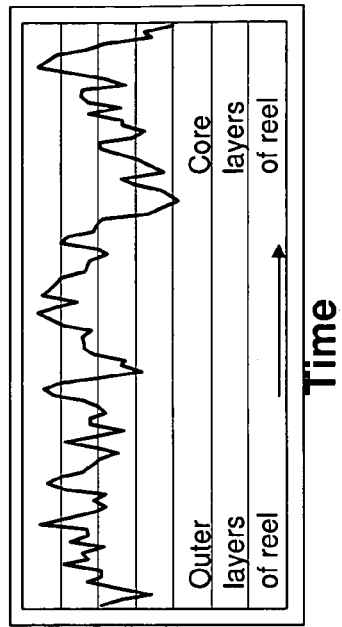
FIG. 4B shows an optical signature of one lane of the reel being produced in the rewinder machine.
Figure 4A:
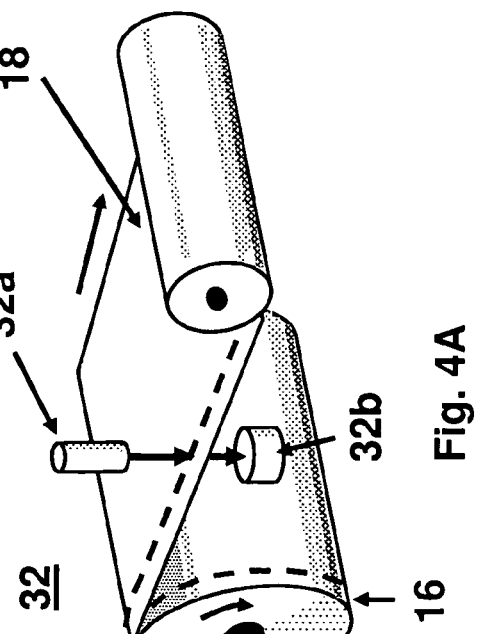
FIG. 4A shows a rewinder with a laser on one side of a moving web and a detector on the other side of the moving web directly below the laser.

As is shown in FIG. 4A, the winder 22 includes an optical transmission sensor 32 of similar design to optical transmission system 26 that is located along the edge 34 of moving web 18 of the reel 16 to be rewound that contains the web defect 14. The sensor 32 has a laser 32a that is located on one side of the moving web 18 and a detector 32b that is located on the other side of the moving web 18 and directly below the laser 32a. As shown in FIG. 6, the winder 22 also includes a drive 36 and a winder pulse tachometer 38.

The sensor 26 on the paper machine 10 and the sensor 32 on the winder 22 are both connected to a computing device 40 such as the personal computer and associated video display 42 shown in FIG. 6. Computing device 40 is capable of high speed data acquisition. The signals from the paper machine sensor 26 and the winder sensor 32 are used by computing device 40 to generate the signatures described above. As is described in more detail below, the computing device 40 is used to compare those signatures to locate the defect 14.

Referring now to FIG. 7, there is shown the embodiment of the present invention in which the signal from a web inspection or measurement system 44 located on the paper machine 10 is used, as is described in detail below, to create the signature stored in the computing device 40. A camera in a web inspection or measurement system 46 located on the winder 22 provides a signal to computing device 40 and is used by that device along with the signature created from system 44 to identify the location of the defect 14 on the rewound web 18.

FIG. 3A illustrates the measurement principle on the paper machine. Information from a camera based web inspection system (not shown in FIG. 3A) or a simple optical transmission sensor 26, preferably consisting of a laser 26a on one side of the web 18 and a detector 26b on the other side of the web 18, generates as illustrated in FIG. 3B an optical signature of one lane 48 of the reel 16 being produced in the paper machine. The optical signature may consist either of a continuous measurement of optical transmission in one cross machine location, or a 2-D pattern of optical transmission in a finite size cross machine area, or a pattern of signal exceptions exceeding a certain threshold level. The measurement resolution and the signal processing is selected to allow for accurate tracking of small-scale paper features at typical machine speeds. The optical signature is stored in the computer 40 shown in FIGS. 6 and 7 and is used in the winder 22 for identification of paper location.

In FIG. 4A, the paper reel 16 is shown in the winder together with a second optical sensor 32 of similar design as the optical sensor 26 on the paper machine shown in FIG. 3A. As the paper 18 is rewound into rolls, the signal from the sensor 32 as illustrated in FIG. 4B is essentially the same as the signal on the paper machine 10, but it is played in reverse, operating at a different speed, and it may be truncated at the ends due to lost paper. The invention utilizes a real time cross correlation mathematical operation between the signature from the paper machine 10 and the signature on the winder 22 to translate the paper machine reel coordinates to the winder 22. This mathematical operation allows for a precise knowledge of the web defect location before it visibly appears in the web 18 during the re-winding operation.

By using this knowledge of the web defect location continuously and in advance of the defect visibly appearing in the web surface as the web 18 is rewound between the reel 16 and the roll 24, the speed controls of the winder 22 can be automated to slow down and stop at a position where the defect 14 is accurately positioned and exposed for the operators to repair it.

The correlation from machine 10 to winder 22 must be performed in a position coordinate system rather than on a time sampled basis, due to non-linear time scaling for different speeds of the machine 10 and the winder 22 and start/stop acceleration phases for the winder 22, and the paper machine 10 may also operate with speed changes throughout a reel 16.

There are three basic solutions to this correlation requirement. They are:

1) Perform the camera or sensor signature sampling at equidistant position intervals in the web machine direction. The interval between the samples can for instance be chosen to be exactly 1 mm. This can be accomplished by using the machine drive pulse tachometers 28 and 38 shown in FIGS. 6 and 7 to continuously update the sampling rate to be proportional to the tachometer pulse rate. This synchronization to web motion may be accomplished by one of several techniques well known to those of ordinary skill in the art such as driving the signature acquisition clock by the tachometer pulse train, or a phase locked loop tied to the tachometer, or by a software routine periodically updating signature acquisition speed to track the tachometer frequency.

2) Operate the camera or sensor signature acquisition on a fixed clock basis, with subsequent translation of the time based sensor data array to a position based signature data vs. machine position coordinate array by storing the tachometer frequency as a time dependent variable and re-mapping sensor data per position unit in post processing.

3) Position stamping each recorded sheet signature information element with a position number corresponding to the elapsed sheet travel distance using the pulse tachometer information, for instance with 1 mm resolution.

For continuous signature measurement, the data collection at typical rates will generate large data sets for the duration of a reel 16. For instance, a single channel optical sensor sampling continuously at a 20 kHz rate for a reel duration of 40 minutes generates 48 mega samples per reel or 96 to 192 Megabytes of data. This is not an unrealistic PC memory demand since modern PC's 40 can for low cost be equipped with large capacity memory. However, there are signal-processing schemes to reduce the amount of data that needs to be stored and processed. One approach is to only save data that exceeds a certain threshold level, while selecting the threshold level so signature data is still recorded at frequent intervals, for instance during 10% of the time.

Another approach to reduce the amount of data is to keep the most recent information on the paper machine (for instance, 60 seconds of data) in a FIFO buffer and only selectively process and store the information before, during and after the defect occurrence if the sheet inspection alarms that a defect 14 passes through the inspection system 12 or 44. The resulting pattern around the defect location will be the basis of a subsequent pattern recognition search by cross correlation in the winder 22. The length of the truncated data array must still be sufficient to generate an early warning in the winder 22 in order to slow down and stop the winder 22 without overshoot at the defect 18.

The pattern recognition method for the simple case of a single point optical transmission sensor such as for example the sensor 26 with laser 26A and detector 26B shown in FIG. 3A, can utilize cross correlation of the prior recorded signal from the paper machine 10 and the real time signal in the winder 22. The cross correlation function will be at a maximum at the actual machine direction position shift from the machine to the winder 22, and this serves to determine the machine direction sheet coordinate location of the defect 14 in the winder 22. The general cross correlation function for two signals x(t) and y(t) has the well known form:

$$R_{xy}(t) = \int_{-\infty}^{\infty} (x(\tau) \times y(t+\tau)) d\tau$$

Figure 5A:
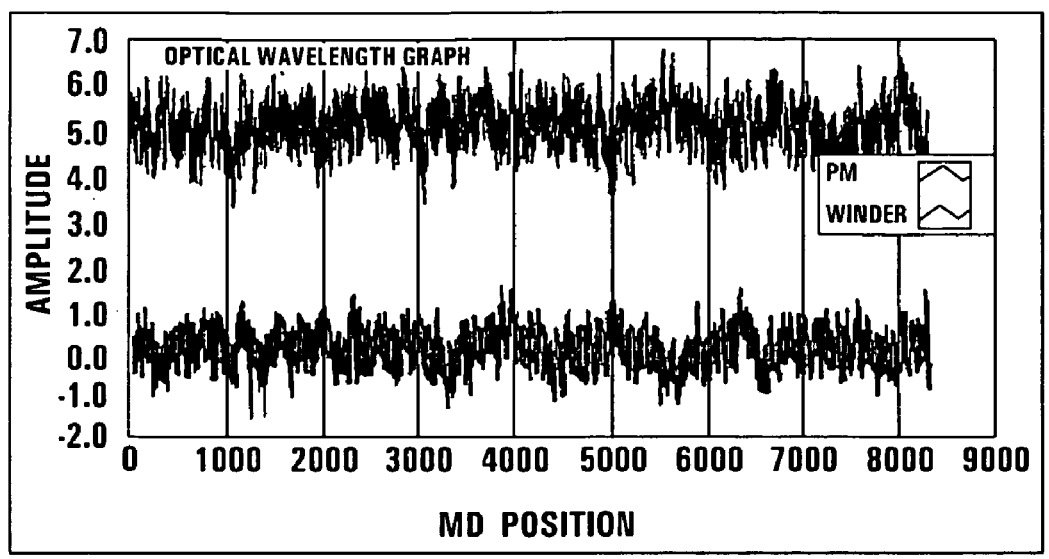
FIG. 5A shows the result of a LabVIEW simulation of two measurement signatures of the same physical specimen, shifted in time and with high frequency and low frequency noise added between the two different measurement events.
Figure 5B:
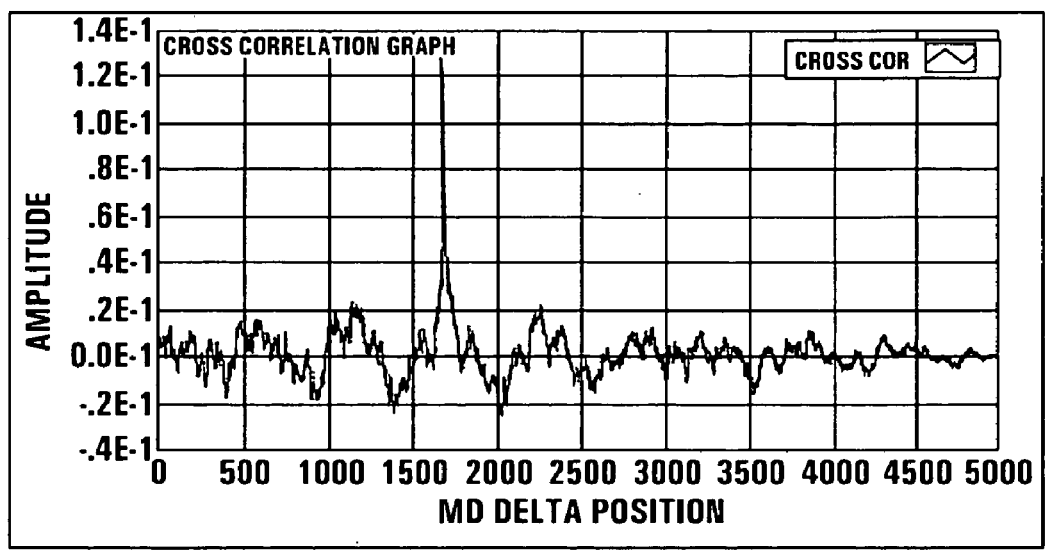
FIG. 5B shows the cross correlation of the two signatures shown in FIG. 5A.

FIG. 5A shows the result of a LabVIEW simulation of two measurement signatures of the same physical specimen, shifted in time and with high frequency and low frequency noise added between the two different measurement events. The upper signal shown in FIG. 5A is the measurement signal from the winder 22 and the lower signal shown in that figure is the measurement signal from the paper machine 10. FIG. 5B shows the cross correlation function for these signals. The correlation peak visibly occurs at the proper signal delay but there is a limit on how much noise is tolerated to get satisfactory results. There are additional methods well known in the art, including pre-filtering, drift restoration and slope normalization, to make the method more robust in the presence of noise or measurement changes.

A general purpose cross correlation equation handling large arrays can be too time consuming for this purpose, and tighter boundary conditions and/or faster processing methods may be necessary to enable the cross correlation. Knowledge about the paper machine 10 and winding operation 22 must be added to include only realistic conditions inside the boundaries, and furthermore, the tachometer signal generated "footage counter" on both the paper machine 10 and the winder 22 should be utilized to augment the optical correlation. In addition, existing reel diameter measurements may be added. The added constraints assist to make the correlation method more robust and practical for real time utilization.

In order to establish the cross correlation between signatures by web inspection cameras, such as those in systems 44 and 46 shown in FIG. 7, measuring the same finite area in the cross direction on the paper machine 10 and the winder 22, the same cross basic correlation rules apply. The location of the correlation peak and thus synchronizing coordinates between the paper machine 10 and the winder 22 is established by establishing a maximum in a signature pattern matching algorithm.

There are different methods to establish the correlation of a camera established 2-dimensional sheet signatures. One example of such a method is described below.

This method is based on minimizing a cost function defined by utilizing the difference between:
1. a video signal measured, processed and stored during the product making process; and
2. a video signal measured and processed by one standard camera, such as the camera used in a web inspection system (WIS) sold by ABB, during rewinding.

This method is especially suitable for web products which have random base texture like paper, metals etc.

The processing of the video signal during the product making process includes the following steps:
1. compensating for the MD speed differences of the product making process and the rewinding,
2. compensating for the differences of the viewing areas of the cameras in the CD direction,
3. requantizing the video signal range to optimize authentic phase mark generation,
4. possibly generating a video difference signal (for example the difference of pixels in CD direction with a chosen distance), and
5. generating, after completion of the processing described above, a sequence of the processed video signal values.

An optimal product phase marking method is dependent on the video signal to be used for marking and in some cases the usage of the video difference signal in the cross direction of the web 18 or in the machine direction of the web 18 with specified pixel distances identifies the marks more optimally. The video difference signal includes the information of the relationships between neighboring pixels and thus the spatial video frequencies defined by the specified pixel distances are emphasized in the phase marks. In this way, the a priori information of the spatial frequencies of the original video signal can be utilized in optimization of the phase marking.

Automatic video signal analysis can be utilized in the optimization of the requantization process. The generated sequence of the processed video signal values is used as a phase mark. The sequence can include processed unidimensional (CD direction) or two-dimensional (CD and MD directions) video signals and possibly video difference signals. The phase mark can be selected from a larger area to have best separation characteristics, i.e., the greatest deviation. The area size depends on the MD rate of stored phase marks. The phase mark is stored with the corresponding MD position value (MD phase). The MD rate of the stored phase marks defines the resolution of the phase synchronization during rewinding.

During the rewinding, the video signal value sequences are measured and processed to compare them to the stored sequences, i.e., the phase marks, by utilizing a specific cost function. The match between the stored sequences and the measured and processed video signal value sequences during rewinding can be found by minimizing the result of the cost function.

With this method all that is needed for the control of the automatic braking system during the rewinding is to add one standard WIS camera and I/O devices in addition to a WIS such as that now sold by ABB.

The steps described above for the processing of the video signal from the one standard WIS camera during the product making process are now described in detail.

MD Product Making and Rewinding Speed Difference Compensation

The original corrected (flat field corrected) video signal from the one standard WIS camera is MD filtered to compensate for the MD speed difference between the product making and the rewinding processes. The larger the speed difference, the lower is the cutoff frequency needed for the MD lowpass filtering for the video signal measured from the slower of the product making and rewinding processes. The lowpass filter can be based on a simple infinite impulse response (IIR) structure. The normalized first order IIR filter for the MD filtering can be given by $$\text{vid}_{LP_{MD}}(n) = b \text{vid}_{corr}(n) + (1-b)\text{vid}_{LP_{MD}}(n - L_{scan}), \tag{1}$$

where b is the filter coefficient. The same filtering structure can be utilized in both the product making and rewinding processes.

Compensation of the Difference of the Viewing Areas of the Product Making and Rewinding Cameras in the CD Direction The difference of the size of the viewing areas of the cameras of the product making process and the rewinding process is compensated by scaling the CD sizes of the pixels. The smaller viewing area can be scaled by the lowpass filtering and the resampling in the CD direction. CD filtering can be based on window averaging. An averaged signal $\text{vid}_M(p)$ is calculated by a spatial window mask running over the source video signal $\text{vid}_{LP_{MD}}(i)$.

The averaged signal for video signal sequence generation can then be given by $$vid_M(p) = \frac{1}{2L}\left[\sum_{i=p-L}^{p+L-1} vid_{LP_{MD}}(i)\right], \tag{2}$$

where L is the local window length (the whole window length is then 2L). The same filtering structure can be utilized in both processes in case of need. The resampling uses the interpolation technique during the video sequence (the phase mark) generation.

Video Difference Signal Generation

The video difference if needed is used to improve the separation characteristics of the phase marks in the product making and the rewinding processes. Therefore, if the video difference is used it is calculated after the speed and/or viewing area difference compensations. The video difference signal can be given by $$\text{diff}_M(p) = \text{vid}_M(p) - \text{vid}_M(p+d), \tag{3}$$

where d is the distance between pixel values in the CD direction.

Requantization of the Video Signal Range

Requantization means reducing the quantization levels of the video signal to reduce the amount of information and to reach better separation and reliability of the phase marks.

Automatic video signal analysis can be utilized in the optimization of the requantization process. For example, maximum/minimum filtering, statistical analysis or extreme value search of signals can be utilized in the definition of the thresholds of the requantization. Requantization can be nonlinear.

An example of requantization can be given by $$vid_{rq}(p) = \begin{cases} 3, & \text{if } vid_M(p) > th_1 \\ 2, & \text{if } vid_M(p) > th_2 \\ 1, & \text{if } vid_M(p) > th_3 \\ -1, & \text{if } vid_M(p) < th_4 \\ -2, & \text{if } vid_M(p) < th_5 \\ -3, & \text{if } vid_M(p) < th_6 \\ 0, & \text{otherwise,} \end{cases} \quad (4)$$

where $th_1$-$th_6$ are threshold values, which can be adjusted manually and/or automatically. The thresholds (for example 3 threshold values in the light side and 3 values in the dark side of the video signal) can be updated in real-time having target values which causes the desired percentage of pixel values to be exceeded by the specified threshold.

One objective is to have enough quantization levels inside the standard deviation of the video signal and the other objective is to have some quantization levels to represent extreme values of the video signal. The optional video difference signal $diff_M$ can also be requantized or the difference signal can be calculated from the requantized video signal $vid_{rq}$.

Generation of a Sequence of the Video Signal Values

A sequence of the processed video signal values is used as a phase mark. The sequence can include processed unidimensional (CD direction) or two-dimensional video signals and possibly video difference signals. The phase mark can be selected from a larger area (as described above the area size depends on the MD rate of the stored phase marks) to have the best separation characteristics, i.e., the greatest deviation. The phase mark is stored with the corresponding MD position value (MD phase). The MD rate of the stored phase marks defines the resolution of the phase synchronization during rewinding.

An example of the sequence of the processed video signal values can be given by $$seq_M(i) = [vid_{rq}(i), vid_{rq}(i+1), \ldots, vid_{rq}(i+ss-1)], \quad (5)$$

where ss is the size of the sequence.

The resampling of the requantized video signal in the CD direction is applied during the phase mark generation. As described above in the compensation of the difference of the viewing areas of the product making and rewinding process cameras, the resampling is for the compensation of the difference of the size of the viewing areas of those cameras.

Cost Function Definition for the Difference Between Video Sequences

As previously described, during the rewinding the video signal value sequences are measured and processed to compare them to the stored sequences, i.e., the phase marks, by utilizing a specific cost function. The match can be found by minimizing the result of the cost function. The cost function for the difference between the stored video value sequence and the current video value sequence in the rewinder can be given by $$diff_{seq_M seq_{rew}}(p) = \sum_{i=0}^{ss-1} (\text{abs}(seq_M(i) - seq_{rew}(i+p))), \quad (6)$$

where $seq_M$ is a video sequence stored during the product making process, $seq_{rew}$ is a video sequence read in the rewinder and p is the CD position of the video sequences in the rewinder. It should be appreciated that the cost function described above is one example of a cost function. Other cost functions may be used, such as using least squares to calculate vector distances which may be more accurate than the above described cost function, but require more computing power than that cost function.

To ensure the synchronization in the CD direction, the cost function can be calculated in several CD positions and the minimum result is selected for the matching analysis. The minimum value can be derived from $$diff_{min}(p) = \min(diff_{seq_M seq_{rew}}(p-syn), diff_{seq_M seq_{rew}}(p-syn+1), \ldots, diff_{seq_M seq_{rew}}(p+syn)), \quad (7)$$

where syn is the parameter for the CD synchronization. The cost function can be calculated in 10 one CD position if the position of the phase mark is known exactly using some a priori information.

MD Phase Synchronization

The whole reel could be divided into smaller areas, which include several marks. The MD phase of the rewinding process can be found by searching the minimum value of the cost function inside the product area under consideration.

MD Resolution of the Phase Synchronization

The MD resolution of the phase synchronization is based on the density of the phase marking in MD.

Testing of the Method

The method is tested with the image material simulating different imaging configurations of the product making process and the rewinding process. Several different MD speeds, light levels, viewing areas and light sources are used during testing.

Figure 8:
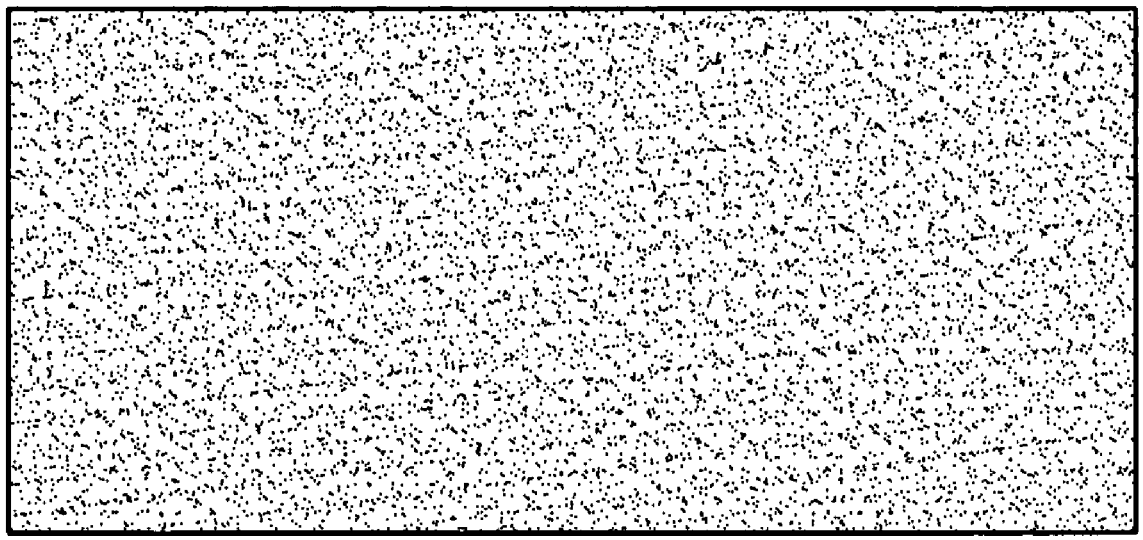
FIG. 8 shows the original image from a web inspection system simulating the original video signal of the web making process.
Figure 9:
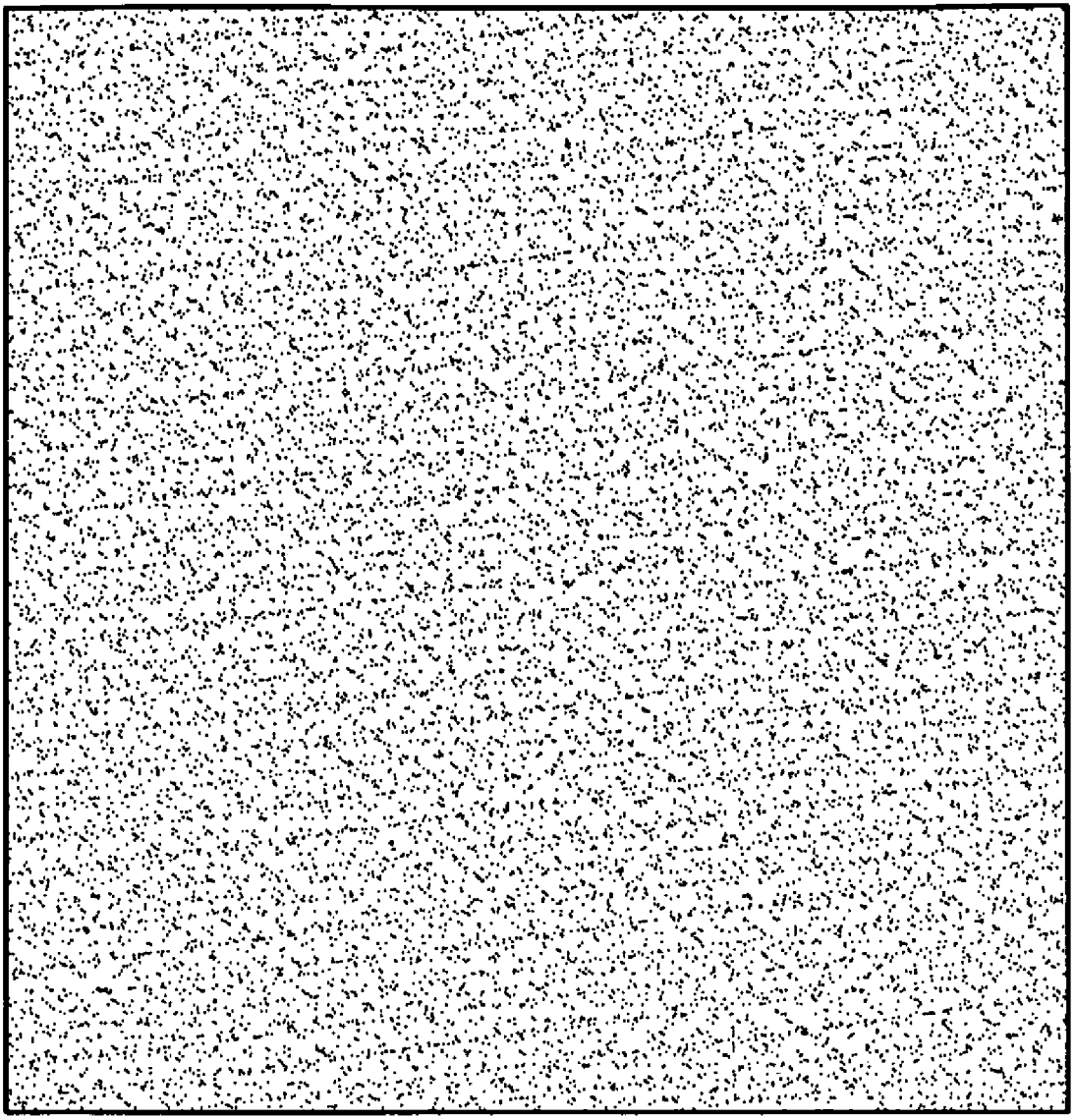
FIG. 9 shows the corresponding image simulating the original video signal for the rewinding process.

An example of the testing of the product phase marking is shown in FIGS. 8-13. The original image simulating the original video signal of the product making process is shown in FIG. 8. The MD speed of the product is 468 m/min, a led light source is used for the lighting and scan time is 84 μs. The corresponding image simulating the original video signal of the rewinding process is shown in FIG. 9. In this case, the same product is imaged by using the halogen lighting, 110 m/min MD speed and 42 μs scan time.

Figure 10:
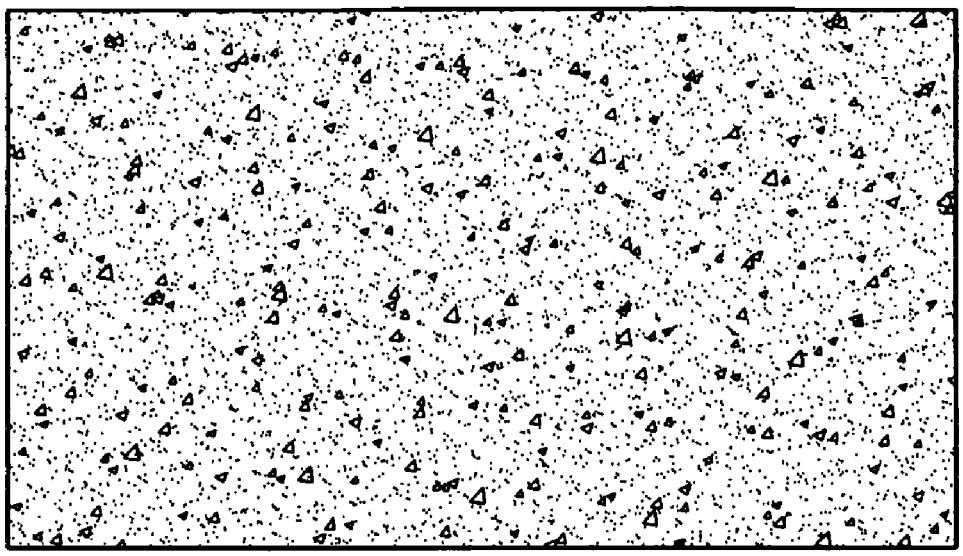
FIGS. 10 and 11 show the images of FIGS. 8 and 9, respectively, after compensation for the machine direction (MD) speed differences, the cross direction (CD) viewing area differences and requantization.
Figure 11:
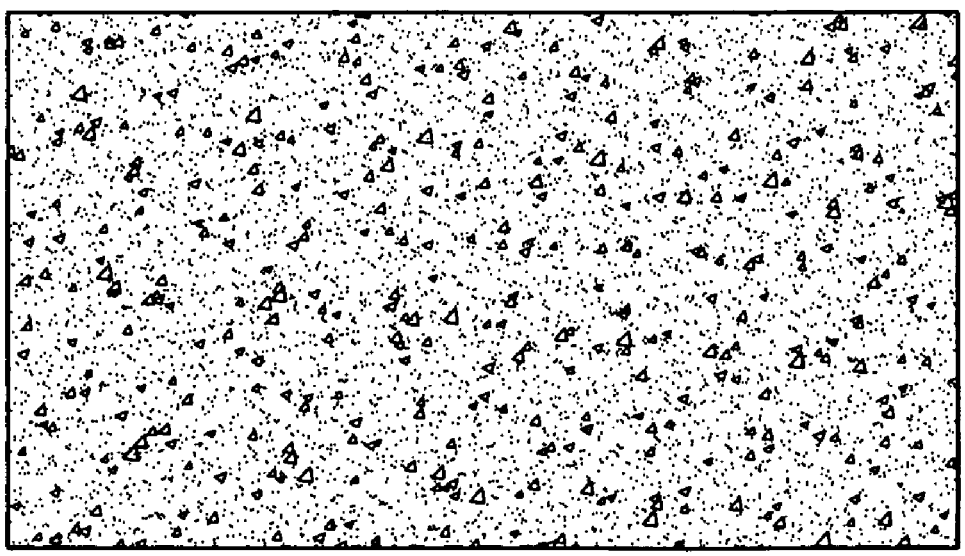

The same images after the compensation for the MD speed differences, the CD viewing area differences and the requantization are shown in FIGS. 10 and 11. In this case, the linear requantization is used which is not optimal.

Figure 12:
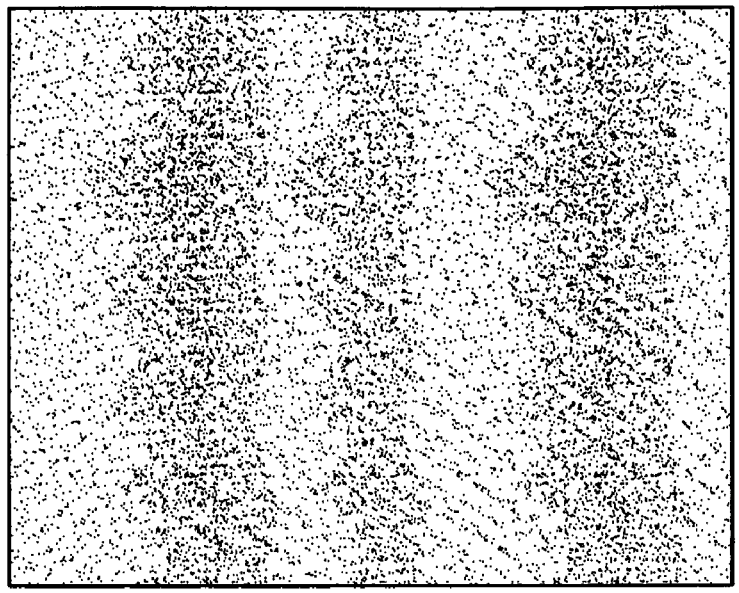
FIG. 12 illustrates the cost function result that is to be minimized by the embodiment of the present invention associated with the images shown in FIGS. 8-11.
Figure 13:
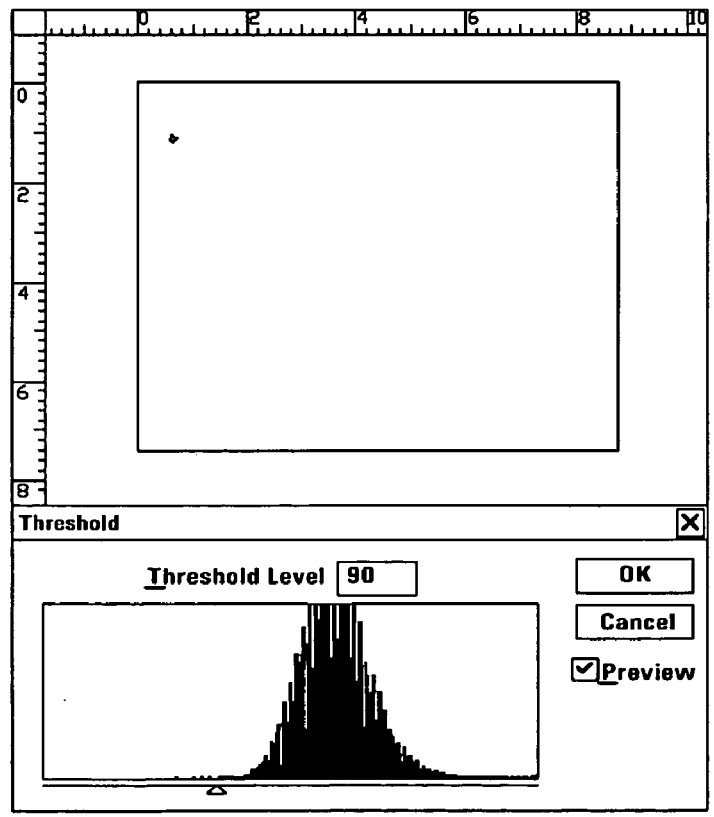
FIG. 13 illustrates one example of the thresholding of the cost function.

FIG. 12 illustrates the cost function result when the phase mark is stored using 128 video values of FIG. 10 (starting from the top of that figure). A clear minimum area of the cost function can be seen around the position (20,30), where 20 and 30 are the horizontal and vertical pixel positions in FIG. 10, respectively, with the origin placed in the upper left corner of FIG. 10. The phase mark corresponding to the minimum of the cost function is calculated from pixels 20 . . . 20+128 in line 30 of FIG. 10. An example of the thresholding of the cost function is shown in FIG. 13.

Another example of such a correlation method is described below.

The key principle of this method is to estimate the machine direction (MD) position of the running sheet 18 in measurement point B, given the measurement data of the same sheet in measurement point A. The measurement at point A occurs in time before the measurement B. In measurement A, the MD position of the sheet 18 is known with adequate precision. The task is to transfer the MD position information to measurement B without marking the sheet material itself.

In between the two measurement points, the sheet travel direction may be reversed due to the rewinding of the reel 16. Also the sheet 18 may be cut clean at either or both of the ends in order to remove damaged paper from the reel and the rewound rolls of paper at the winder. This cutting of the sheet is sometimes referred to as slabbing. The amount of removed paper at either end may vary greatly from reel to reel. The sheet 18 may also stretch or shrink in the machine direction due to tension or stress relaxation in the winding operation causing a length change. All of these phenomena are to be taken into account when performing non-contact MD position information transfer from the first measurement to the second measurement.

The method described herein is based on two cameras measuring the properties of the sheet-like material at the two consecutive points A and B. The method is to record short spatially continuous areas of the sheet in so-called snapshot images. The snapshot images are used for calculating discriminative properties of the sheet material, which can later be used as key points in locating the current MD position. Storing and comparing all individual images would be impractical due to the vast amount of data in each image and the large number of images representing a reel of paper. Therefore, each image is reduced to a set of discriminative properties, which serve as condensed descriptors of the two-dimensional image.

The discriminative properties for each image can be used to track locations of the web throughout the conversion process, but without the need to store the full content of individual images. Paper making generates random fiber flocs, thin areas and defects that appear as local dark or light areas in each image. The details of this dark and light pattern are unique for each image. The discriminative properties for each image can for instance be a set of numbers that describe the relative locations and intensity of the most outstanding light and dark areas within the camera field of view. In order to provide these descriptors, the image must be generated with sufficient resolution to reveal typical dark and light areas.

The discriminative properties for each image in conjunction with standard cross-correlation techniques can be utilized for estimating the most likely current MD position at measurement point B. The continuous or semi-continuous nature of the sheet movement can be utilized for restricting and filtering the output of the estimation process.

The matching of the discriminative properties can be carried out also using methods other than cross-correlation and can be run on-line for a sheet under production as well as off-line for two sheets already measured. The off-line mode can be utilized in situations, when the same sheet is measured twice or more after different production stages to combine measured material data, like visible defects or other quality information. The on-line mode can be used, for example, for stopping the sheet at the exact position for taking corrective measures.

The discriminative properties derived from the snapshot images are preferably illumination invariant and focus invariant as long as the focus of the cameras is adequate for calculating the properties. Illumination invariance is achieved by selecting illumination invariant filters, like the LBP, or by pre-amplifying the images to constant mean and constant variance. The image dimensions and resolution should be selected so that the scale of the features makes image features generated by cameras on the paper machine and on the winder more or less focus invariant. All features based primarily on spatial relationships of distinctive parts or areas of the signal should be preferred over features that rely on absolute intensity properties of the filtered or unfiltered signal. Given the nature of any sheet material, only affine transformation should be possible between any two measurement points, and the transformations are likely to be linear and in the machine direction only, like the above mentioned reduction.

The method can be carried out by assembling two cameras at positions A and B seeing essentially the same cross-directional zone. Camera A records images substantially shorter and more frequently than those recorded by camera B. It is required that the long snap shot images of camera B cover at least two imaging intervals of camera A to assure that a sheet portion representing the image from camera A will always be seen in full by camera B.

For these images a fingerprint procedure is carried out. The fingerprint for each image is defined by defining relative threshold levels in the image and identifying the five brightest or darkest areas resulting in five key areas per image. The relative threshold levels are defined by adjusting dark and bright side threshold levels closer and closer to the background formation level until only five key areas exist. As the threshold levels are adjusted symmetrically, the remaining areas can be all from dark or all from the bright side or any combination of dark and bright areas.

To avoid noise and sampling related inaccuracies between two measurement points, it is advantageous to set a minimum area limit for key areas to be accepted. In this manner, singular pixels or very small areas are discarded, thus avoiding the problems raising from the different spatial quantization of the measurement signal at points A and B. The minimum area for the key areas should always be at least four original un-scaled pixels to overcome the abovementioned problem and more if different spatial resolutions are used in points A and B or if there are significant differences in focus of the cameras.

Relative position vectors (RPVs) are calculated between all key areas resulting in ten RPVS per image. An RPV is calculated as the angle relative to machine direction and distance between two key areas. The coordinates of a key area are defined as the darkest or brightest point of a dark or bright area, respectively. In the presence of many equally dark or bright pixels the average position of the points is selected as the key area position. As the direction of the vector is unimportant, only the length and unsigned angle of the vector is preserved for the matching stage. Unsigned angle is the angle between the undirected vector, or line segment, and machine direction chosen from the range of [0, Pi).

The method described herein works well even in the presence of substantial additive noise. This is due to the immensely descriptive power of two-dimensional spatial co-occurrence, i.e. the superposition of the key areas. The probability of getting a false positive indication of spatial co-occurrence with three points, corresponding to three RPVs, using one pixel spatial accuracy inside an image is given as:

$$P_f = !k/(W*H)^{-k-1},$$

where W is the width and H is the height of the image and k is the number of co-occurring points.

With an image size of 128×128 and three points this gives a false positive probability of $2.2*e^{-8}$, i.e. by average every $44^{th}$ million indication is falsely positive. It should be noted though, that one pixel accuracy can not be implemented in practice. In the practical case the false positive probability can be calculated as $$P_f = !k/(W'^* H')^{k-1},$$

where W' and H' are the quantized image width and height, given respectively by $$W' = (W - r_w)/r_w \text{ and } H' = (H - r_h)/r_h$$

where $r_w$ and $r_h$ are the spatial accuracies, width and height, in pixels.

With a spatial accuracy of four pixels in both directions, there is obtained a practical false positive probability of roughly $6.5 * e^{-6}$, i.e. 1/154000. With four points and six RPVs, there is obtained a practical false probability of $2.7 * e^{-8}$ or 1 per 37 million which is more than enough for any practical use. The false positive accuracy of the procedure can be further improved by using labeled points and directed vectors.

By labeling the points for example to BLACK (B) and WHITE (W) based on whether the detection is from the dark or bright side, the accuracy is considerably improved. Labeled points result in three types of RPVs, each of which can be searched within its own manifold only: BB, BW and WW. With labeled points also directed vectors can be utilized resulting in four types of RPVs, each of which can be searched within its own manifold only: BB, BW, WB and WW. This reduces the computational search effort and also increases matching accuracy. In order to utilize the full improvement of the labeled point usage, it is advantageous force the threshold level setting procedure to produce at least two key areas from both sides, dark and bright. As the description of an area with aforementioned parameters is almost unique within one sheet, the RPV set of an image can fairly called its finger print. The chance of getting a similar set of RPVs from the same sheet is negligible.

Estimating the MD Position Based on Image Finger Prints

RPVs of images from camera A are searched for from the RPVs of images from camera B. Any matching RPVs found from the images of camera B indicate that the images of camera B are from the same MD position as the respective images of camera A, which have a known MD position. The more matching RPVs are found, the higher the probability, that the images are retrieved from the same position in the measured sheet. This search procedure enables the MD position estimation at measurement position B.

Any MD positions retrieved using the aforementioned procedure are fed to a regulated extrapolator, which based on the available tachometer input and MD positions retrieved from camera A calculates an estimate of current MD position at measurement position B. The calculated MD position estimates are regulated on the assumption of monotonically increasing MD position, i.e. there is no reversing or backward movement of the sheet during production, and given maximum slabbing length and maximum acceleration speeds. The regulations make it less likely for the estimator to update the position faster than physically possible or in the reverse direction, although this can not be totally banned, as it is possible, that all previous estimates have been incorrect. It is not necessary to give further details of the estimator because building different types of well behaving estimators is very well documented in the prior art. A use of a Kalman filter as an estimator is an adequate solution, as it also incorporates the measurement noise estimation into the estimation loop.

Figures

Figure 14A:
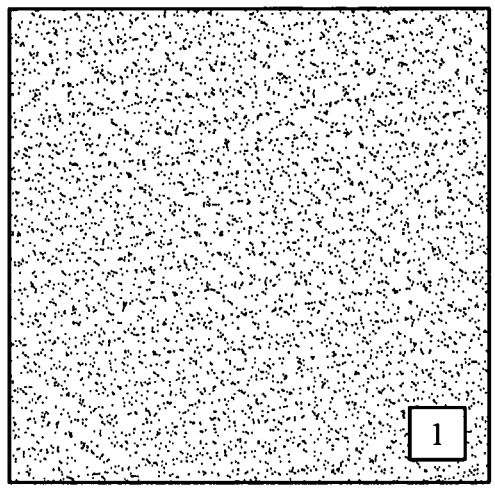
FIG. 14a to 14h show snapshot images of a paper web in accordance with another embodiment of the present invention.
Figure 14B:
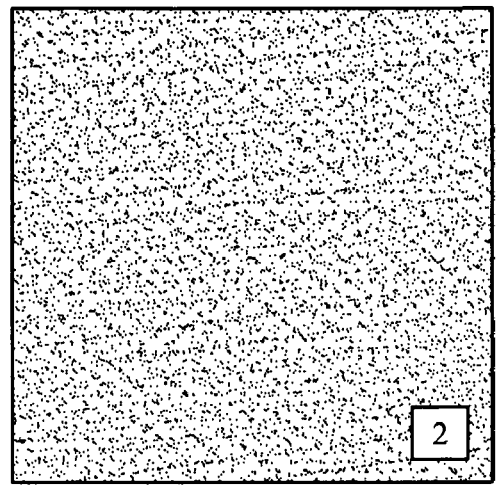
Figure 14C:
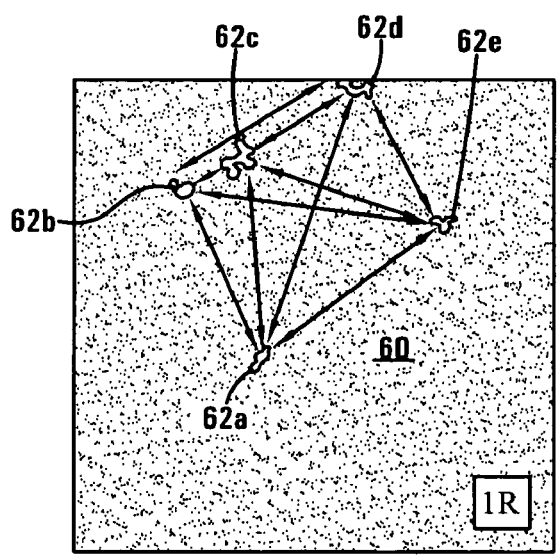

The images shown in FIGS. 14a to 14h illustrate the invention utilized on four snapshot images of a transmission illuminated paper web. The images have different grey scale variation or grey scale mean or the image is captured with varying illumination condition or a small amount of noise has been added to the original image. All images have been analyzed with the procedure described above and the results have been visualized in the images labeled with 'R'. The result image of sample 1 shown in FIG. 14a, that is, image 1R shown in FIG. 14c, shows all ten relative position vectors (RPV) collectively identified as 60 for the five most significant finger print areas 62a, 62b, 62c, 62d and 62e marked with the dark borderlines in the image. The finger print areas 62a to 62e are selected in this example to be the dark flocs, i.e. clumps of fiber, and the five most significant areas are selected based on size.

Figure 14D:
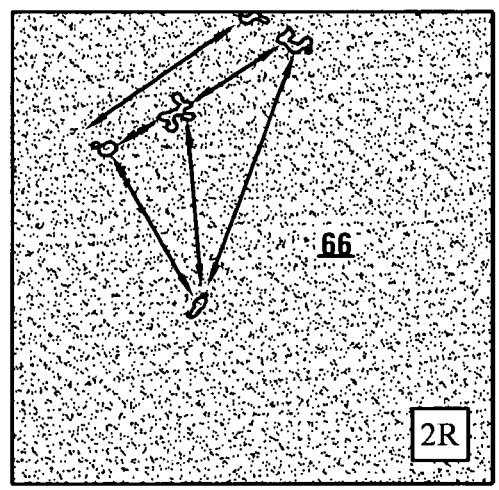
Figure 14E:
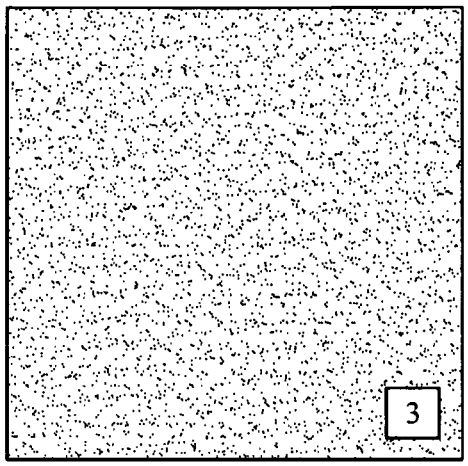
Figure 14F:
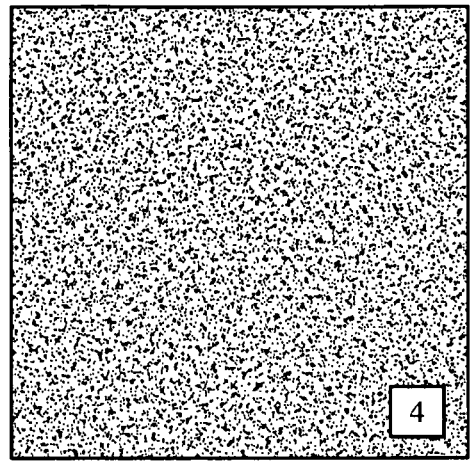
Figure 14G:
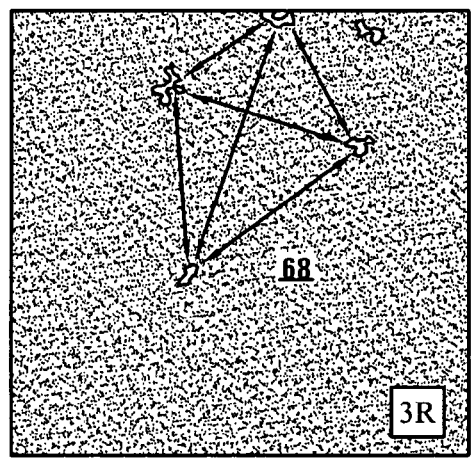

Three consecutive result images 1R-3R shown in FIGS. 14c, 14d and 14g, respectively, show only RPVs similar in distance and angle to any of the RPVs 60 of sample 1.

Finding at least three RPVs out of ten can be considered as adequate for giving a reasonable confidence level for assuming that the samples are from the same sheet position. These example images demonstrate that the method of the present invention is invulnerable to variations in grey scale mean and variations as well as small additions of process independent noise.

Figure 14H:
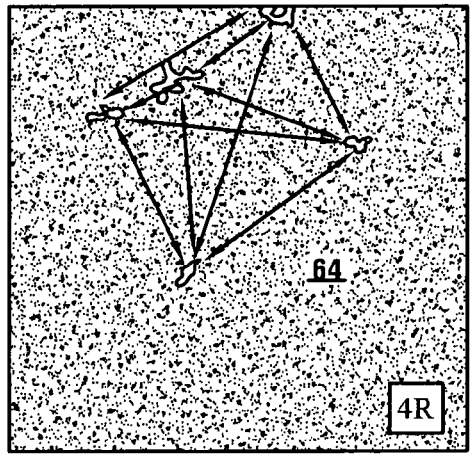

FIGS. 14a to 14h are artificially altered images of the same origin, thus representing possible disturbances and variations between two different measurement points imaging the same sheet position. The figures illustrate the applicability of the invention in the presence of such disturbances and variations. A person skilled in the art realizes, that although a great amount of independent noise has been applied to the original signal, image 1, the method still works. FIGS. 14c and 14h respectively for images 1R and 4R have similar RPVs 60 and 64 respectively, as the areas found, although not identical are located in the same positions. This happens although the variance of the images is considerably different. FIGS. 14d and 14g respectively for images 2R and 3R show subsets of RPVs 66 and 68 respectively of the images 1R and 4R, because additive measurement noise (generated) has altered the positions of the five key areas. Still, adequate amount of common key areas remain for reliable identification of the same sheet location.

In accordance with the present invention, control schemes can be built for automatic stopping at a defect using predetermined ramp-down and ramp-up rates to provide a soft stop and start, while wasting no time to search for the precise location of a defect. This helps to improve winder efficiency and reduce the chance of building up paper machine reels in a queue which is a frequently occurring problem in the prior art manual search for the actual defect location.

The invention is not limited to positional correlation between a paper machine and a winder. Other applications include using the method for example in a coater, where the coater blades may need to be timed precisely and lifted when a pre-determined defect is going to pass, or there may be a sheet break.

An additional added value feature possible in the present invention is to use the optical signals on the paper machine to continuously generate a high-speed machine diagnostics function with mathematical analysis of true machine direction variability which is not possible on a scanner unless it is parked on a single point and the scan pattern is interrupted. In the embodiments described herein that use sheet inspection cameras for obtaining sheet signatures, additional sheet variability information can be obtained by similar processing of the data sets.

As can be appreciated the present invention has additional variations including using non-optical sensors or surface reflection sensors for measuring the machine direction process signature on at least two locations—as long as the two chosen sensors have essentially identical measurement results.

As will be appreciated by one of skill in the art, the present invention may be embodied as a method, system, or computer program product. Accordingly, the present invention may take the form of an entirely hardware embodiment, an entirely software embodiment (including firmware, resident software, micro-code, etc.) or an embodiment combining software and hardware aspects.

Furthermore, the present invention may take the form of a computer program product on a computer-usable or computer-readable medium having computer-usable program code embodied in the medium. The computer-usable or computer-readable medium may be any medium that can contain, store, communicate, propagate, or transport the program for use by or in connection with the instruction execution system, apparatus, or device and may by way of example but without limitation, be an electronic, magnetic, optical, electromagnetic, infrared, or semiconductor system, apparatus, device, or propagation medium or even be paper or other suitable medium upon which the program is printed. More specific examples (a non-exhaustive list) of the computer-readable medium would include: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a transmission media such as those supporting the Internet or an intranet, or a magnetic storage device.

Computer program code for carrying out operations of the present invention may be written in an object oriented programming language such as Java, Smalltalk, C++ or the like, graphical languages such as LabVIEW, or may also be written in conventional procedural programming languages, such as the "C" programming language. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through a local area network (LAN) or a wide area network (WAN), or the connection may be made to an external computer (for example, through the Internet using an Internet Service Provider).

It is to be understood that the description of the foregoing exemplary embodiment(s) is (are) intended to be only illustrative, rather than exhaustive, of the present invention. Those of ordinary skill will be able to make certain additions, deletions, and/or modifications to the embodiment(s) of the disclosed subject matter without departing from the spirit of the invention or its scope, as defined by the appended claims.

What is claimed is:

1. A system for locating a defect of a moving sheet having naturally varying properties during first and second sheet making processes, said system comprising:
    a processor capable of executing code stored on a non-transitory medium, said code configured to:
    process a first digital representation of one lane of a reel produced from said moving sheet during said first sheet making process and a second digital representation of said one lane of said reel during said second sheet making process;
    obtain from said first digital representation a first pattern of the naturally varying properties of said moving sheet during said first sheet making process;
    obtain from said second digital representation a second pattern of the naturally varying properties of said moving sheet during said second sheet making process; and
    locate said sheet defect during said second sheet making process by correlating said first and said second patterns.

2. The system of claim 1 wherein said first and said second patterns each comprise an optical signature consisting of a continuous measurement of the optical transmission of the moving sheet in one location in the cross-machine direction.

3. The system of claim 1 wherein said first and said second patterns each comprise an optical signature consisting of a 2-D pattern of optical transmission in a predefined cross-machine area.

4. The system of claim 1 wherein said first and said second patterns each comprise a pattern of signal exceptions exceeding a predefined threshold level.

5. The system of claim 1 wherein said code is configured to correlate said first pattern to said sheet defect during said first sheet making process to define said sheet defect relative to said first pattern.

6. The system of claim 1 further comprising a machine that performs said first sheet making process.

7. The system of claim 6 further comprising a machine that performs said second sheet making process.

8. The system of claim 1 further comprising a machine that performs said first and said second sheet making processes.

9. The system of claim 1 wherein said system further comprises a first system for generating said first digital representation and a second system for generating said second digital representation.

10. The system of claim 9 wherein said first system for generating said first digital representation and said second system for generating said second digital representation each comprise a sheet inspecting system selected from the group consisting of optical sheet inspection systems and sheet sensor systems.

11. A method for tracking features of a moving sheet having naturally varying properties, the method comprising:
    detecting a defect in said sheet during a first sheet making process;
    obtaining a first pattern of the naturally varying properties of said sheet during said first sheet making process;
    obtaining a second pattern of the naturally varying properties of said sheet during a second sheet making process; and
    locating said defect during said second sheet making process by correlating said first and said second patterns.

12. The method of claim 11 wherein said first and said second patterns each comprise an optical signature consisting of a continuous measurement of the optical transmission of the moving sheet in one location in the cross-machine direction.

13. The method of claim 11 wherein said first and said second patterns each comprise an optical signature consisting of a 2-D pattern of optical transmission in a predefined cross-machine area.

14. The method of claim 11 wherein said first and said second patterns each comprise a pattern of signal exceptions exceeding a predefined threshold level.

15. The method of claim 11 further comprising, correlating said first pattern to said defect during said first sheet making process to define said defect relative to said first pattern.

16. A computer program product stored on a non-transitory media for tracking features of a moving sheet having naturally varying properties, said computer program product comprising:
- computer usable program code configured to obtain a sheet defect signal during a first sheet making process;
- computer usable program code configured to obtain a first pattern of the naturally varying properties of said moving sheet during said first sheet making process;
- computer usable program code configured to obtain a second pattern of the naturally varying properties of said moving sheet during a second sheet making process; and
- computer usable program code configured to locate said sheet defect during said second sheet making process by correlating said first and said second patterns.

17. The computer program product of claim 16 wherein said first and said second pattern comprises an optical signature consisting of a continuous measurement of the optical transmission of the moving sheet in one location in the cross-machine direction.

18. The computer program product of claim 16 wherein said first and said second pattern comprises an optical signature consisting of a 2-D pattern of optical transmission in a predefined cross-machine area.

19. The computer program product of claim 16 wherein said first and said second pattern comprises a pattern of signal exceptions exceeding a predefined threshold level.

20. The computer program product of claim 16 further comprising computer usable program code configured to correlate said first pattern to said sheet defect during said first sheet making process to define said sheet defect relative to said first pattern.

* * * * *